United States Patent [19]

Drinkard et al.

[11] Patent Number: 5,321,155
[45] Date of Patent: Jun. 14, 1994

[54] PROCESS FOR THE PRODUCTION OF CYCLOHEXYLADIPATES AND ADIPIC ACID

[75] Inventors: William C. Drinkard, Wilmington, Del.; Gerald C. Grunewald, Orange, Tex.

[73] Assignee: E. I. Du Pont de Nemours and Company, Wilmington, Del.

[21] Appl. No.: 46,912

[22] Filed: Apr. 15, 1993

[51] Int. Cl.$^5$ ............................................. C07C 51/27
[52] U.S. Cl. .................................. 562/524; 560/193; 560/233
[58] Field of Search ................ 560/193, 233; 562/524

[56] References Cited

U.S. PATENT DOCUMENTS 3,564,051  2/1971  Haarer et al. ...................... 562/524

FOREIGN PATENT DOCUMENTS 51-36267  10/1976  Japan .................................. 560/193
1402480  8/1975  United Kingdom ................ 562/524

*Primary Examiner*—James H. Reamer

[57] ABSTRACT

Cyclohexyladipates are produced by reacting a mixture containing a major amount of benzene and minor amounts of cyclohexene, adipic acid and an acid catalyst.

9 Claims, No Drawings

PROCESS FOR THE PRODUCTION OF CYCLOHEXYLADIPATES AND ADIPIC ACID

FIELD OF THE INVENTION

This invention relates to the production of cyclohexyladipates by the reaction of a mixture containing benzene, cyclohexene and adipic acid to form a mixture of mono- and di-cyclohexyladipates (called herein cyclohexyladipates), and also to the conversion of the thus formed cyclohexyladipates to adipic acid by nitric acid oxidation.

BACKGROUND OF THE INVENTION

A conventional method for the manufacture of adipic acid is the air oxidation of cyclohexane to form a mixture of cyclohexanone and cyclohexanol. This mixture is then oxidized with nitric acid to adipic acid.

The preparation of adipic acid is also carried out commercially by the selective hydrogenation of benzene to form cyclohexene, separation of the cyclohexene from the unconverted benzene and the over-hydrogenated cyclohexane by extractive distillation, then hydration of cyclohexene to form cyclohexanol, and the nitric acid oxidation of the cyclohexanol to adipic acid. See for example Kagaku Kogaku (Chemical Technology), vol. 55, No. 5, pp 382-385 (1991); "Technology for Manufacturing Cyclohexanol using Cyclohexene Technique" by Shikazo Senoo and Koji Nakagawa.

British Patent 1,402,480 teaches the preparation of adipic acid by esterification of cyclohexene with adipic acid using an acid catalyst, and then oxidizing the cyclohexyladipates with nitric acid to form adipic acid.

Japanese published patent application 51-36,267 (Published Oct. 7, 1976) discloses that cyclohexyladipates may be formed by the reaction of cyclohexene and adipic acid using an acid catalyst. The published application states: "The cyclohexene used in the present invention may be conventional-grade cyclohexene; the presence of a small amount of inert substances such as cyclohexane and benzene does not present a problem."

SUMMARY OF THE INVENTION

The present invention is a process for the preparation of cyclohexyladipates by the reaction of a mixture containing (a) a major amount of benzene, (b) minor amount of cyclohexene, (c) adipic acid and (d) a catalytic amount of an acid catalyst at a temperature greater than 100 degrees C. and a pressure greater than about 50 psig to form cyclohexyladipates. The cyclohexyladipates may then be separated from the other components by distillation, and the cyclohexyladipates, if desired, may be converted to adipic acid by nitric acid oxidation.

The present invention is thus able to use as the feed stock the reaction material obtained by the partial hydrogenation of benzene. See Drinkard U.S. Pat. No. 3,767,720. No separation of the cyclohexene is required. The present process also eliminates the hydration of cyclohexene to cyclohexanol and cyclohexanone. Furthermore, in the present process after preparation of the cyclohexyladipates by use of acid catalysts, the separation of the cyclohexyladipates from the other components is simplified. The present invention allows direct nitric acid oxidation of the cyclohexyladipates to form adipic acid.

The process is attractive because of satisfactory conversions and yields: this process operates at 2-20 times the conversion rate of traditional cyclohexane oxidation systems and it has a 10-25% higher yield to adipic acid.

DETAILED DESCRIPTION

There are many known processes for the preparation of cyclohexene by the partial hydrogenation of benzene. The Drinkard patent is an example. Most of the known processes employ ruthenium as a catalyst. These processes produce a reaction mixture containing benzene, cyclohexene and cyclohexane. To avoid the formation of large amounts of cyclohexane, it is necessary to operate the processes at benzene conversions of about 50% or less, which results in a selectivity to cyclohexene of as high as about 80%, and a selectivity to cyclohexane of about 20%. If less benzene is converted, the selectivity to cyclohexene is greater. For the process of the present invention a feed stream of about 80% benzene, 18% cyclohexene, and 2% cyclohexane is preferred.

In accordance with the present invention, a feed stream containing major amounts of benzene, and minor amounts of cyclohexene is reacted with adipic acid in the presence of a catalytic amount of an acid catalyst. Preferred acid catalysts include acidic silica alumina, tin tetrachloride, zinc dichloride, vanadium oxide ($V_2O_4$), p-toluenesulfonic acid, and acid ion exchange resins such as Nafion. Both Lewis acids and Bronsted acids may be satisfactory. A preferred Lewis acid is zinc dichloride. The amount of catalyst needed will usually be in the range of about 1-100 parts per million parts of the reaction mixture. The adipic acid in the reaction mixture should be present in at least a stoichiometric amount necessary to form the mono-cyclohexyladipate. Excess adipic acid is often desirable. Some di-cyclohexyladipate will form even at high ratios of adipic acid to cyclohexene.

The phrase "major amount of benzene" means that benzene is present in the reaction mixture in an amount substantially in excess of the amount of cyclohexene. Thus the phrase "minor amount of cyclohexene" means that cyclohexene is present in the reaction mixture in an amount substantially less than the amount of benzene. Normally the ratio of benzene to cyclohexene in the reaction mixture is in the range of about 3 to 1 to about 6 to 1. The reaction mixture will normally also have 1 to 10% by weight cyclohexane.

The formation of the cyclohexyladipates is carried out at a temperature above about 100 degree C. Temperatures as high as 210 degrees C. are satisfactory.

The cyclohexyladipate-formation process step is carried out under pressure. Pressures greater than 50 psig are required. Pressures up to 200 psig are satisfactory.

After formation of the cyclohexyladipates, the benzene and cyclohexane are separated from the reaction mixture. Simple distillation is a satisfactory means of separation. Distillation at about 80-100 degrees C. and at a pressure of about 0-5 psig is satisfactory. The mixture of benzene and cyclohexane taken overhead may be recycled to a partial hydrogenation process. The bottoms containing the cyclohexyladipates are then oxidized with nitric acid. The nitric acid oxidation can be carried out in the same reactor and under the same conditions that are usually employed for the oxidation of cyclohexanone and cyclohexanol in the formation of adipic acid: i.e. the nitric acid concentration is about 20 to 80% and the reaction temperature is about 40 to 120 degrees C. (See British patent 1,402,480 page 3 column 2 for details).

It is contemplated that the process be carried out where the production of cyclohexyladipates and the separation of this product from the unreacted benzene and cyclohexane are done in the same reaction vessel as part of a reactive distillation step. Such a concept has the added advantage of further process simplification.

EXAMPLE

A 60 ml stainless steel autoclave is charged with the following mixture: 10.0 g of benzene, 8.0 g of cyclohexene, 2.0 g of cyclohexane, 15.0 g of adipic acid, and 40 mg of $ZnCl_2$. This system is heated to 130 deg. C. at an initial cold pressure of 50 psig for 1 hour. 3.0 g of cyclohexyladipates were formed.

The entire reaction mixture is distilled at atmospheric pressure at 83 deg. C. which separates the unreacted benzene, cyclohexene, and cyclohexane from the higher boiling cyclohexyladipates and unreacted adipic acid. This tails mixture of cyclohexyladipates and adipic acid is oxidized with $HNO_3$ to convert to entirely adipic acid.

A semimicro oxidation flask (50 ml) fitted with a serum stoppered feed point, thermometer, condenser, magnetic stirrer and heating mantle was charged with 20 ml (27.21 g) of 58% nitric acid (0.5% Cu, 0.5% V). This charge was spiked with about 5 mg sodium nitrite and heated to 85° C. then 1.502 g of cyclohexyladipates (68% mono-cyclohexyladipate, 32% di-cyclohexyladipate) was injected below the stirred liquid surface over a 17 minute period at a temperature of 86° C. (+ or −1° C.). The 85° C. temperature was held 10 minutes after ester addition was completed then the solution temperature was quickly increased to 98°–100° C. and held for 5 minutes.

The product was analyzed and the yield to dibasic acids was determined by subtracting the adipic acid content of the esters form the total adipic acid in the product in order to determine the moles of adipic formed by oxidation of the cyclohexyl portion of the esters. The yield to adipic acid was 95% with 3.5% glutaric acid and 1.5% succinic acid. This yield is equivalent to the yield obtained in a similar nitric oxidation using cyclohexanol and cyclohexanone as a feed rather than cyclohexyladipates.

We claim:

1. A process for the production of cyclohexyladipates which comprises (a) forming a reaction mixture containing a major amount of benzene, and a minor amount of cyclohexene, adipic acid and a catalytic amount of an acid catalyst, and (b) reacting said mixture at a temperature above about 100 degrees C. and at a pressure greater than about 50 psig to form cyclohexyladipates.

2. The process of claim 1 in which the reaction mixture also contains cyclohexane.

3. The process of claim 1 in which the acid catalyst is selected from the group consisting of Bronsted and Lewis acids.

4. The process of claim 1 in which the acid catalyst is an acidic cation exchange resin.

5. The process of claim 4 in which the acid catalyst is a Lewis acid and the Lewis acid is zinc dichloride.

6. The process of claim 1 in which the cyclohexyladipates are a mixture of mono and di-cyclohexyladipates.

7. A process for the production of adipic acid which comprises (a) forming a reaction mixture containing a major amount of benzene, a minor amount of cyclohexene, adipic acid and a catalytic amount of an acid catalyst, (b) reacting said mixture at a temperature above about 100 degrees C. and at a pressure greater than about 50 psig to form cyclohexyladipates, (c) separating the cyclohexyladipates from the other components by distillation, and (d) oxidizing the cyclohexyladipates to adipic acid by nitric acid oxidation.

8. The process of claim 1 in which the adipic acid is present in the reaction mixture in an amount at least stoichiometrically equivalent to the amount of cyclohexene.

9. The process of claim 1 in which the reaction mixture contains benzene and cyclohexene in a ratio of about 3 to 1 to about 6 to 1.

* * * * *